(12) United States Patent
Grady et al.

(10) Patent No.: US 11,605,466 B2
(45) Date of Patent: Mar. 14, 2023

(54) SYSTEMS AND METHODS FOR ASSESSMENT OF TISSUE FUNCTION BASED ON VASCULAR DISEASE

(71) Applicant: HeartFlow, Inc., Redwood City, CA (US)

(72) Inventors: Leo Grady, Millbrae, CA (US); Charles A. Taylor, Atherton, CA (US)

(73) Assignee: HeartFlow, Inc., Redwood City, CA (US)

( * ) Notice: Subject to any disclaimer, the term of this patent is extended or adjusted under 35 U.S.C. 154(b) by 1325 days.

(21) Appl. No.: 15/991,097

(22) Filed: May 29, 2018

(65) Prior Publication Data

US 2018/0277254 A1    Sep. 27, 2018

Related U.S. Application Data

(63) Continuation of application No. 15/099,165, filed on Apr. 14, 2016, now Pat. No. 10,007,762.

(60) Provisional application No. 62/149,145, filed on Apr. 17, 2015.

(51) Int. Cl.
| | | |
|---|---|---|
| *G16H 50/50* | (2018.01) | |
| *A61B 5/02* | (2006.01) | |
| *A61B 5/026* | (2006.01) | |
| *A61B 5/055* | (2006.01) | |
| *A61B 5/00* | (2006.01) | |
| *G06T 7/00* | (2017.01) | |
| *G16H 10/60* | (2018.01) | |
| *A61B 5/0275* | (2006.01) | |
| *A61B 5/053* | (2021.01) | |
| *A61B 5/11* | (2006.01) | |
| *A61B 5/22* | (2006.01) | |

(52) U.S. Cl.
CPC ......... *G16H 50/50* (2018.01); *A61B 5/02007* (2013.01); *A61B 5/0263* (2013.01); *A61B 5/055* (2013.01); *A61B 5/7275* (2013.01); *G06T 7/0012* (2013.01); *G16H 10/60* (2018.01); *A61B 5/0275* (2013.01); *A61B 5/053* (2013.01); *A61B 5/1107* (2013.01); *A61B 5/224* (2013.01)

(58) Field of Classification Search
None
See application file for complete search history.

(56) References Cited

U.S. PATENT DOCUMENTS

| | | |
|---|---|---|
| 8,315,812 B2 | 11/2012 | Taylor |
| 8,824,752 B1 | 11/2014 | Fonte et al. |
| 2005/0187461 A1 | 8/2005 | Murphy et al. |
| 2013/0179884 A1 | 8/2013 | Mansi |
| 2014/0114618 A1 | 4/2014 | Fonte et al. |
| 2014/0249399 A1 | 9/2014 | Sharma et al. |
| 2014/0249784 A1 | 9/2014 | Sankaran et al. |
| 2014/0249790 A1 | 9/2014 | Spilker et al. |
| 2015/0038860 A1 | 2/2015 | Fonte et al. |
| 2015/0242589 A1 | 8/2015 | Neumann |
| 2015/0347709 A1 | 12/2015 | Mansi |
| 2015/0371437 A1 | 12/2015 | Mansi |
| 2016/0210435 A1 | 7/2016 | Neumann |
| 2016/0220311 A1 | 8/2016 | Mansi |

FOREIGN PATENT DOCUMENTS

WO    WO 2011/124385 A1    10/2011

OTHER PUBLICATIONS

International Search Report and Written Opinion for corresponding Application No. PCT/US2016/027552 dated Jun. 21, 2016 (17 pages).

*Primary Examiner* — Lori A. Clow
(74) *Attorney, Agent, or Firm* — Bookoff McAndrews, PLLC (57) ABSTRACT

Systems and methods are disclosed for assessing tissue function based on vascular disease. One method includes receiving a patient-specific anatomic model generated from patient-specific imaging of at least a portion of a patient's tissue; receiving a patient-specific vascular model generated from patient-specific imaging of at least a portion of a patient's vasculature; receiving an estimate of blood supplied to a portion of the patient-specific anatomic model; and determining a characteristic of the function of the patient's tissue using the estimate of blood supplied to the portion of the patient-specific anatomic model.

20 Claims, 6 Drawing Sheets

SYSTEMS AND METHODS FOR ASSESSMENT OF TISSUE FUNCTION BASED ON VASCULAR DISEASE

RELATED APPLICATION(S)

This application is a continuation of U.S. application Ser. No. 15/099,165, filed Apr. 14, 2016, which claims priority to U.S. Provisional Application No. 62/149,145 filed Apr. 17, 2015, all of which are hereby incorporated herein by reference in their entireties.

FIELD OF THE DISCLOSURE

Various embodiments of the present disclosure relate generally to disease assessment and related methods. More specifically, particular embodiments of the present disclosure relate to systems and methods for assessing tissue function based on vascular disease and/or treatment(s) of the disease.

BACKGROUND

Vascular disease may include an impairment of a patient's blood flow or an irregularity of a patient's circulatory system. For example, the impairment may include blood flow not being sufficient for meeting tissue demand for blood. This insufficient blood flow may lead to impairment of tissue function or patient death. For example, coronary artery disease (CHD) may impair cardiac function, leading to cardiac arrest or death. As another example, peripheral artery disease (PAD) may entail reduced blood flow to limbs, which may cause loss of function of the limb. Clinical techniques for assessing vascular disease may include observing functional compromise due to disease (e.g., percent stenosis, fractional flow reserve (FFR), instantaneous wave-free ratio (iFR), coronary flow reserve (CFR), etc.) or a perfusion deficit (e.g., assessed by single-photon emission computed tomography (SPECT), (positron emission tomography (PET), ultrasound, magnetic resonance (MR) perfusion, computed tomography (CT) perfusion, etc.). However, these clinical tools may be limited because: 1) a diseased vessel may not cause a significant perfusion deficit (e.g., small vessels); 2) in patients with multivessel disease, there may be no clear way to associate a specific vessel disease with a perfusion deficit, except through a population-based vessel territory map; 3) a detected perfusion deficit may not have significant impact on cardiac or muscle function (e.g., depending on location/size of the deficit); or 4) a treatment to revascularize the vascular (e.g., coronary) lumen (e.g., percutaneous coronary intervention (PCI), angioplasty, coronary artery bypass grafting (CABG)) may not restore sufficient blood supply to the heart/muscle to correct an impacted cardiac/muscle function.

Thus, a desire exists to better assess the impact of vascular disease, for example, by determining how vascular disease may impact tissue or organ function and/or how vascular disease may affect a risk of patient death. Furthermore, a desire exists to assess whether a treatment may improve tissue or organ function and/or decrease a likelihood of patient death.

The foregoing general description and the following detailed description are directed to overcoming one or more of the challenges described above. The general description and detailed description are exemplary and explanatory only and are not restrictive of the disclosure.

SUMMARY

According to certain aspects of the present disclosure, systems and methods are disclosed for assessing tissue function based on vascular disease and/or treatments of the disease.

One method includes: receiving a patient-specific anatomic model generated from patient-specific imaging of at least a portion of a patient's tissue; receiving a patient-specific vascular model generated from patient-specific imaging of at least a portion of a patient's vasculature; receiving an estimate of blood supplied to a portion of the patient-specific anatomic model; and determining a characteristic of the function of the patient's tissue using the estimate of blood supplied to the portion of the patient-specific anatomic model.

In accordance with another embodiment, a system is disclosed for assessing tissue function: a data storage device storing instructions for assessing tissue function based on vascular disease; and a processor configured for: receiving a patient-specific anatomic model generated from patient-specific imaging of at least a portion of a patient's tissue; receiving a patient-specific vascular model generated from patient-specific imaging of at least a portion of a patient's vasculature; receiving an estimate of blood supplied to a portion of the patient-specific anatomic model; and determining a characteristic of the function of the patient's tissue using the estimate of blood supplied to the portion of the patient-specific anatomic model.

In accordance with another embodiment, a non-transitory computer readable medium is disclosed for use on a computer system containing computer-executable programming instructions for performing a method of assessing tissue function, the method comprising: receiving a patient-specific anatomic model generated from patient-specific imaging of at least a portion of a patient's tissue; receiving a patient-specific vascular model generated from patient-specific imaging of at least a portion of a patient's vasculature; receiving an estimate of blood supplied to a portion of the patient-specific anatomic model; and determining a characteristic of the function of the patient's tissue using the estimate of blood supplied to the portion of the patient-specific anatomic model.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Vascular disease may put a patient at risk for injury, organ impairment, or even death. For example, coronary heart disease (CHD) may cause impaired cardiac function (e.g., during exercise), cardiac arrest, and/or death. Similarly, peripheral vascular disease may cause fatigue, pain (e.g., in a patient's legs), or loss of function of a limb. Clinical techniques for assessing vascular disease include observing functional compromise due to disease (e.g., once disease symptoms are already present) or a perfusion deficit. However, these clinical tools may be limited because vessels may be diseased without causing a noticeable perfusion deficit (e.g., small vessels), causes of perfusion deficits may be difficult to detect, perfusion deficits may not immediately significantly impact tissue or muscle function, and/or treatments may not restore sufficient blood supply to make up for perfusion deficit.

The present disclosure includes systems and methods that may provide improved treatment planning and efficacy by determining linkages between vascular disease, perfusion deficit, and (electrical and/or mechanical) effect(s) of the perfusion deficit. Additionally or alternatively, the systems and methods permit analysis of whether a vascular disease may affect patient health, or how severely a vascular disease may impact a patient's health. The systems and methods discussed may further permit the physician to virtually assess the effect on vascular output (and risk of patient death) of different treatments or of disease progression to determine a way to treat and manage the patient's health.

Figure 1:
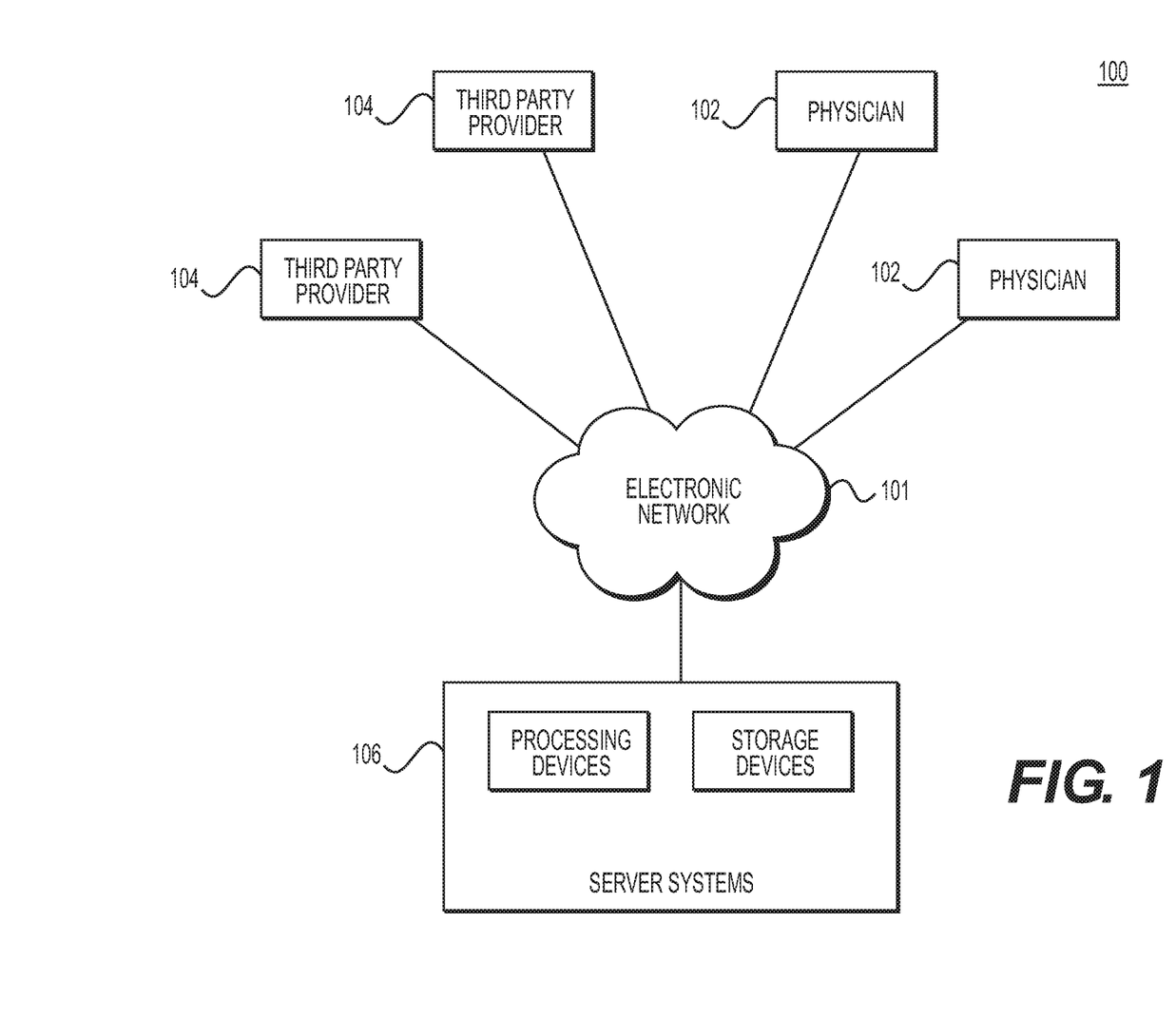
FIG. 1 is a block diagram of an exemplary system and network for assessing tissue function and risk of patient death, especially in relation to coronary artery disease, according to an exemplary embodiment of the present disclosure.

Referring now to the figures, FIG. 1 depicts a block diagram of an exemplary system 100 and network 101 for assessing tissue function and risk of patient death, especially in relation to coronary artery disease, according to an exemplary embodiment. Specifically, FIG. 1 depicts a plurality of physicians 102 and third party providers 104, any of whom may be connected to an electronic network 101, for example, the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, including age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices. For the present disclosure, "patient" may refer to any individual of interest.

Figure 2:
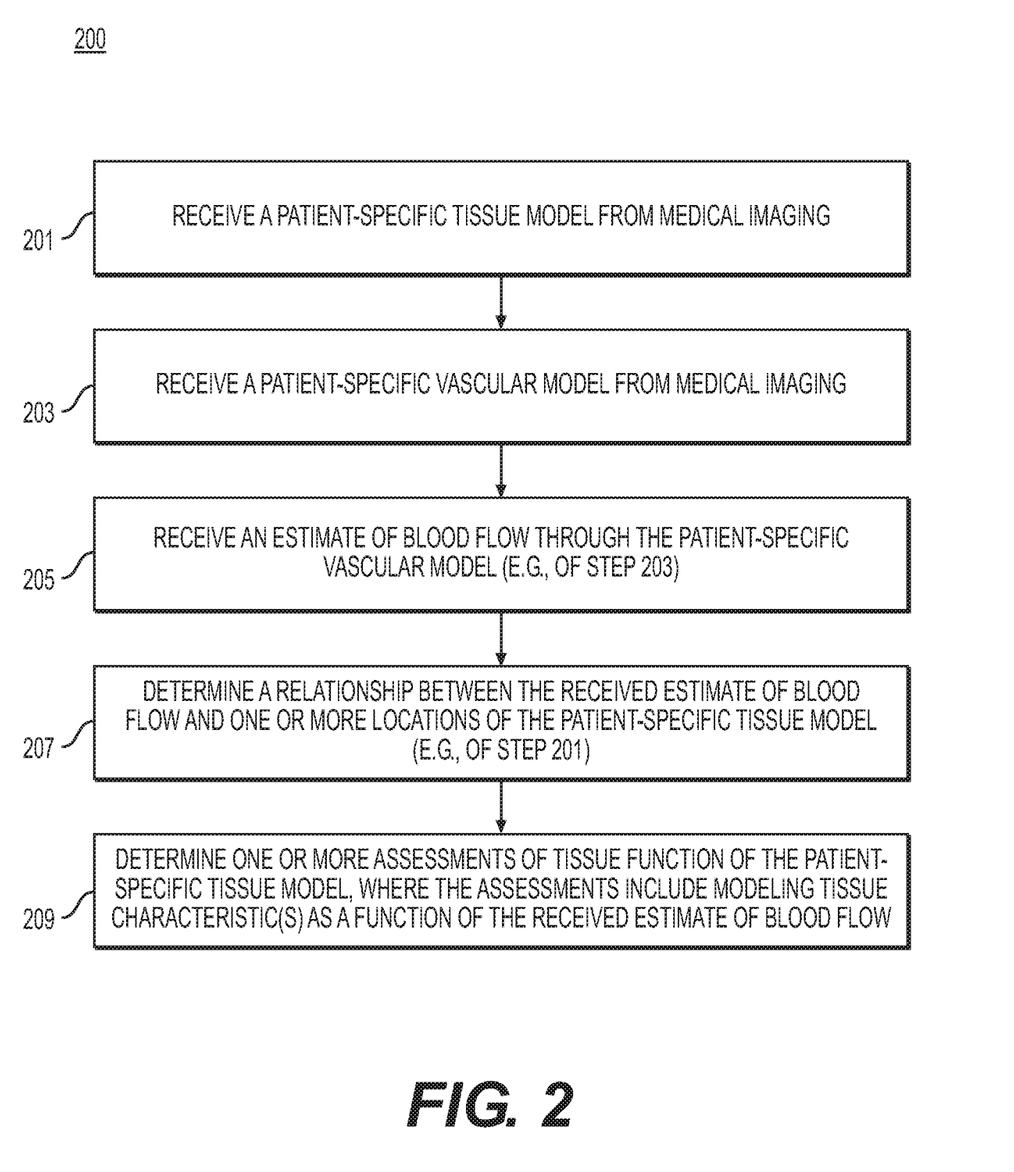
FIG. 2 is a flowchart of an exemplary method of assessing tissue function, according to an exemplary embodiment of the present disclosure.
Figure 3A:
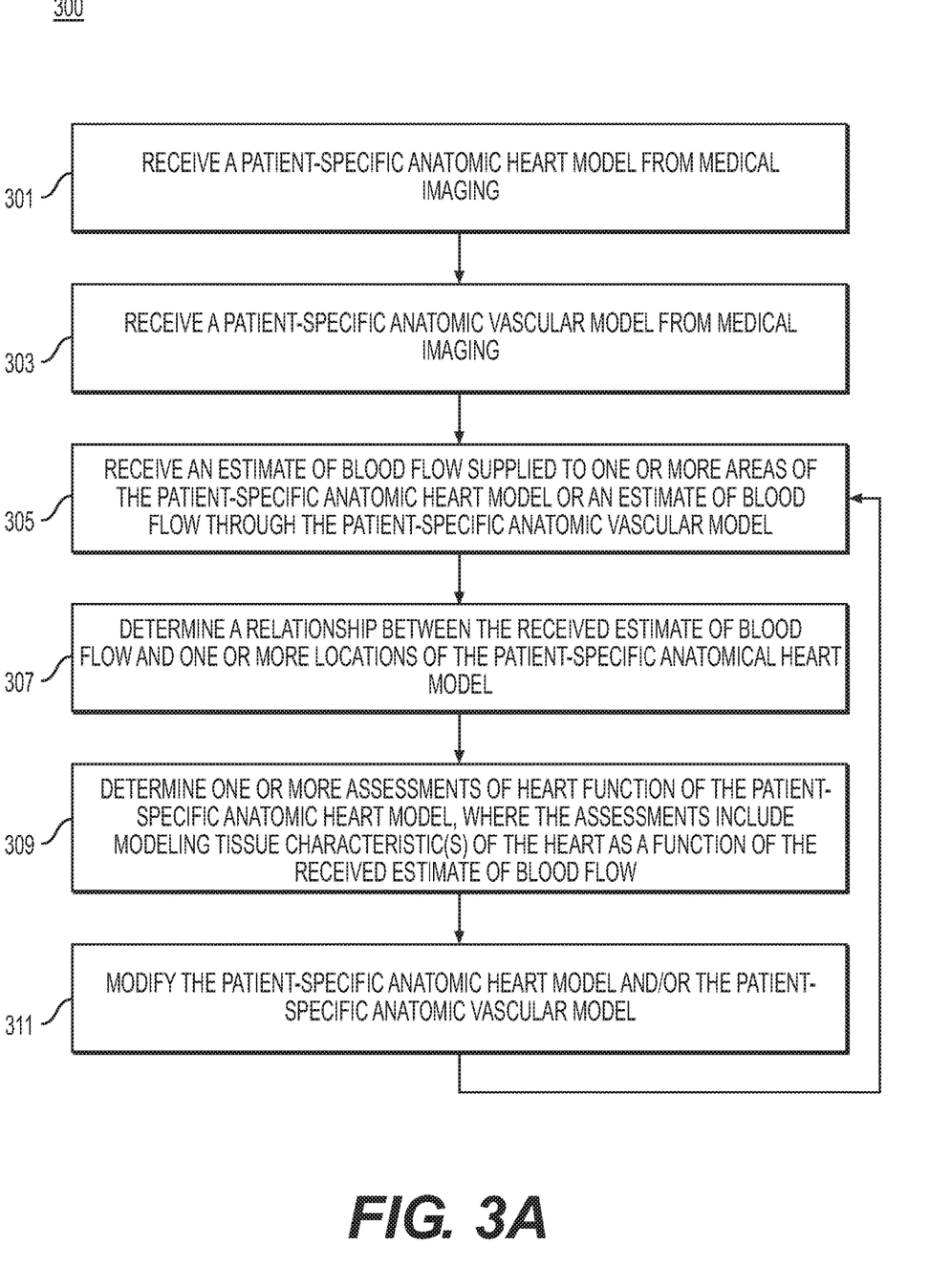
FIG. 3A is a flowchart of an exemplary method of assessing heart function, according to an exemplary embodiment of the present disclosure.
Figure 3B:
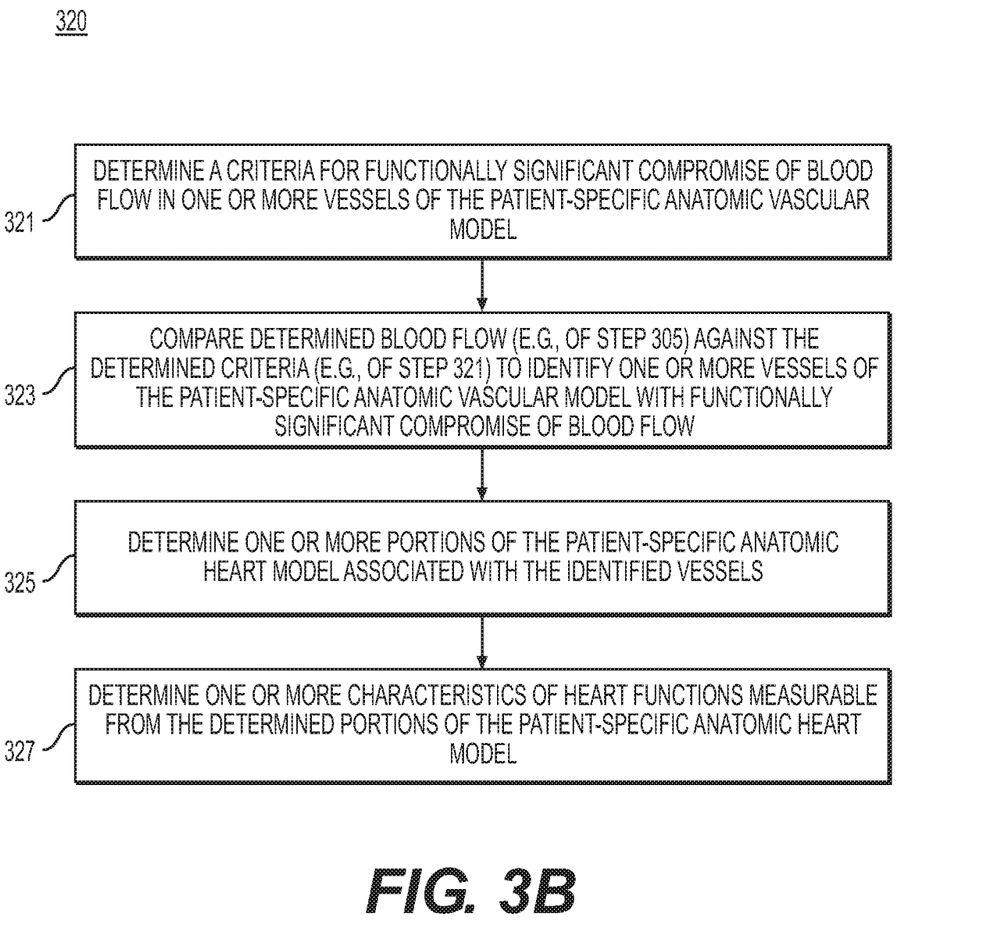
FIG. 3B is a flowchart of an exemplary method of determining portions of the patient's heart (e.g., of the patient-specific heart model) for assessing heart function, according to an exemplary embodiment of the present disclosure.
Figure 4A:
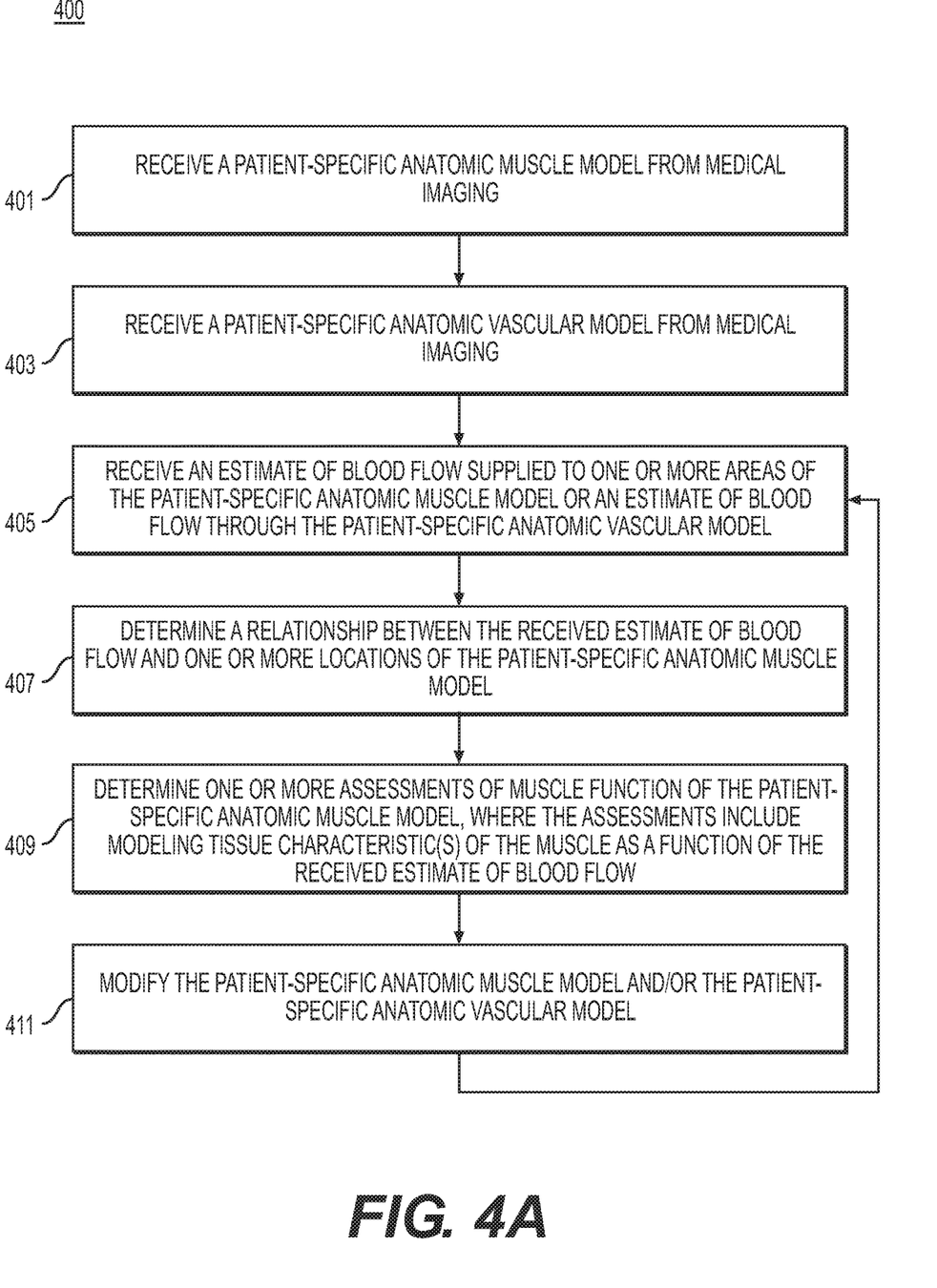
FIG. 4A is a flowchart of an exemplary method of assessing muscle function, according to an exemplary embodiment of the present disclosure.
Figure 4B:
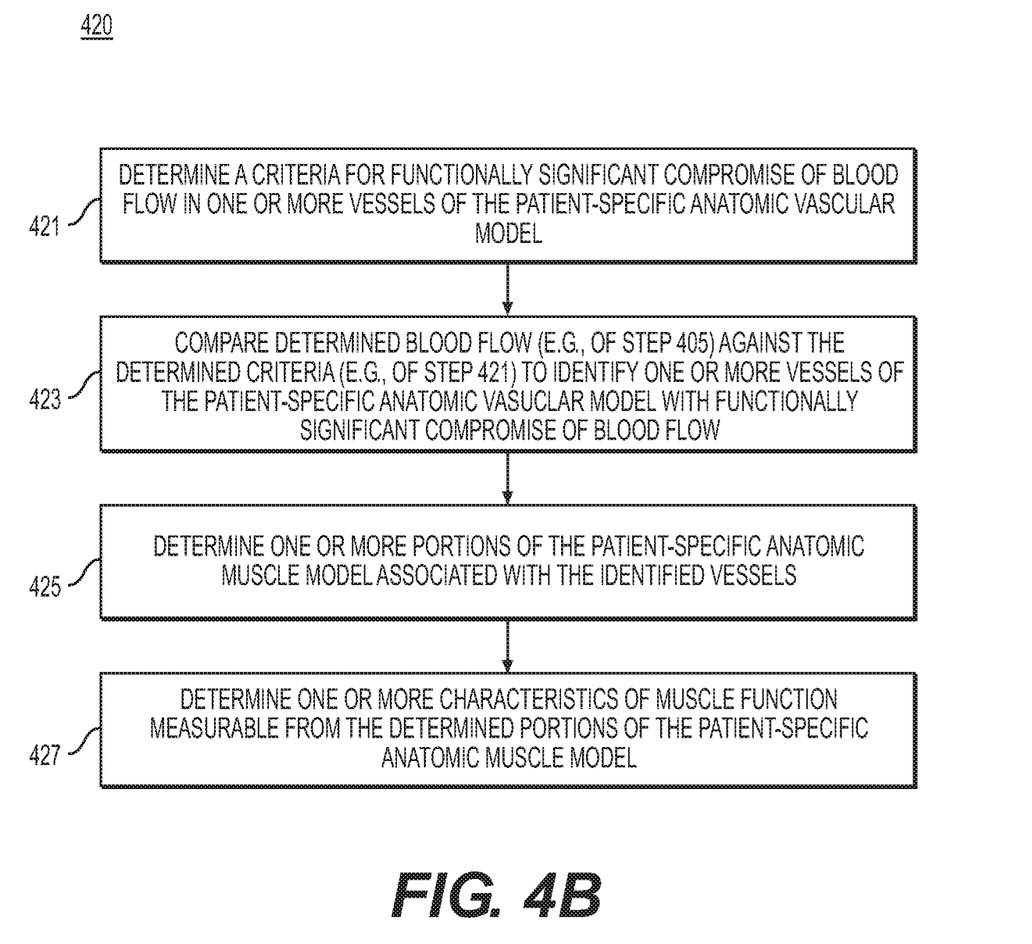
FIG. 4B is a flowchart of an exemplary method of determining portions of the patient's muscle (e.g., of the patient-specific muscle model) for assessing heart function, according to an exemplary embodiment of the present disclosure.

FIG. 2 is a general embodiment for assessing tissue function, and FIGS. 3A and 4A show applied embodiments of the tissue function assessment. For example, FIG. 3A depicts an exemplary flowchart for assessing heart function, and FIG. 4A depicts a flowchart for assessing muscle function. FIG. 3B and FIG. 4B provide more detail to FIGS. 3A and 4A, respectively, by depicting exemplary methods of determining portions of the patient's tissue to assess. FIGS. 3B and 4B provide ways to streamline or reduce the processing time of the methods of FIGS. 3A and 4A, respectively. The exemplary methods of the figures may be performed or used individually, or in any combination. Any or all the steps of the exemplary methods may be performed using a computing processor.

FIG. 2 is a flowchart of an exemplary method 200 of assessing tissue function, according to an exemplary embodiment. The method of FIG. 2 may be performed by server systems 106, based on information, images, and data received from physicians 102 and/or third party providers 104 over electronic network 101.

In one embodiment, step 201 may include receiving a patient-specific tissue model, e.g., in an electronic storage medium. The tissue model may include a three-dimensional anatomic model of a region of tissue of a patient's anatomy. The tissue model may be extracted from medical imaging.

In one embodiment, step 203 may include receiving a patient-specific vascular model, e.g., in an electronic storage medium. The vascular model may include a three-dimensional anatomic model of blood vessels adjacent to or supplying blood to the region of tissue of the tissue model (e.g., of step 201). This vascular model may also be extracted from medical imaging.

In one embodiment, step 205 may include estimating blood flow (e.g., blood flow rate, velocity, quantity, and/or volume) through the patient-specific vascular model, e.g., given a particular physiological state. Estimating blood flow through patient-specific anatomic models may be performed using a method described in U.S. Pat. No. 8,315,812, issued Nov. 20, 2012, the entire disclosure of which is hereby incorporated by reference in its entirety. For example, a patient in a hyperemic physiological state may have a higher blood flow velocity than a patient at a resting physiological state. In one embodiment, step 205 may include determining one or more irregularities in the estimated blood flow. For example, a normal blood flow velocity through a healthy patient's capillaries may be 0.03 cm/s. In one scenario, the vascular model (e.g., of step 203) may include capillaries, and step 205 may include identifying a blood flow irregularity if blood flow through an area of the vascular model deviates from 0.03 cm/s by a certain range. For instance, method 200 may include receiving a definition or criteria of functionally significant compromise of blood flow, and step

205 may include determining the irregularities in the estimated blood flow based on the received definition or criteria of functionally significant compromise of blood flow. A functionally significant compromise of blood flow may include any situation in which a supplied tissue experiences ischemia. Such situations may occur when coronary blood flow supply does not meet tissue demand. For example, normal resting perfusion may range from roughly 0.8 to 1.0 ml/min/g in different patient populations, and stress flow may vary from 1.0 to 5.0 ml/min/g depending on the level of physical activity and the resultant oxygen demands of a patient's working muscle. During rest conditions, values below the normal resting perfusion demand may indicate a compromised resting flow and could elicit rest pain or impair cardiac muscle contraction. During physical activity, values below the expected perfusion for a given level of physical activity may indicate a perfusion deficit and could elicit exertional pain or impair cardiac muscle contraction. For example, a perfusion level of less than 2.0 ml/min/g during maximum exertion may increase risk of a myocardial infarction for a patient. In other words, functionally significant compromise of blood flow may include situations where a patient is impacted by patient blood flow, patient perfusion demand, and/or patient perfusion values falling outside the expected (e.g., normal range) of values.

In one embodiment, step 207 may include determining one or more locations of the tissue model that may be affected by the irregularities in the estimated blood flow. For example, step 207 may include determining locations in the tissue model with blood supply derived from parts of the vascular model associated with compromised blood flow. In other words, step 207 may involve assuming that tissue of the tissue model may be impacted if the tissue is adjacent to the portion of the vascular model with compromised blood flow, since the portion of the vascular model with compromised blood flow is likely not supplying a healthy or expected amount of blood to that tissue. For example, step 207 may include simulating perfusion of blood flow from the patient's vessels to the patient's tissue (e.g., by simulating perfusion of blood flow from the patient-specific vascular model to the patient-specific tissue model).

In one embodiment, calculating perfusion may include isolating a portion of the vascular model to determine a location, or outlet, of one or more vessels of the vascular model. Perfusion may be calculated by dividing the flow from each outlet by an area or volume of tissue (of the tissue model) perfused by the determined vessels of the vascular model. Perfusion may also be calculated by solving for blood flow from the vascular model and/or using a fast marching method, level set method, a diffusion equation, and/or equations governing flow through a porous media. One embodiment may include modeling tissue perfusion volume as static. Another embodiment may include modeling tissue perfusion volume as dynamic, for example, updating the volume using data from coupled cardiac mechanics models.

In one embodiment, step 209 may include determining one or more assessments of tissue function, e.g., for the affected locations of the tissue model. Determining the one or more assessments of tissue function may include selecting, generating, and/or performing assessments of tissue function. For example, step 209 may include assuming that tissue function may be proportional to the blood supply compared to demand (e.g., if 90% of tissue demand is met by blood supplied to that tissue, step 209 may include determining that tissue function of the patient is at 90%). Alternately or in addition, step 209 may include other determinations of tissue function, e.g., nonlinear function(s) of supply (or deficit), and/or a supply deficit cutoff after which tissue function is assumed to be impaired. The assessments may each involve modeling a tissue characteristic as a function of blood flow or supply. The tissue characteristic could be a measure of tissue function. For example, a tissue characteristic of conductance may be modeled as linked to blood supply, where a limited blood supply may cause tissue receiving the blood supply to have reduced electrical conductance. As another example, a tissue characteristic of tissue contractility may be reduced with reduced blood supply to the tissue, as estimated from an assessment of step 209. In the case of cardiac function, an impaired blood supply could result in wall motion abnormalities detectable by echocardiography or magnetic resonance. The assessments of tissue function may further account for such wall motion abnormalities.

In one embodiment, additional steps of method 200 may include modifying any of the models to simulate a virtual treatment or therapy and/or using the modified models to perform an assessment of tissue function, given the virtual treatment or therapy. In one embodiment, tissue function may be compared for various treatment or therapy options. The comparison may provide a determination of a recommended treatment/therapy option for the patient.

In one embodiment, the tissue function, and/or tissue function given various treatments or therapies, may be evaluated over time. For example, the assessments may include determining an immediate consequence of perfusion deficit on a region of tissue and/or prolonged consequences of perfusion deficit. For example, in some areas of the body, perfusion deficit could have little consequence. For instance, if a patient is sedentary, he may not feel a reduction in lower limb blood flow until the reduction in blood flow becomes so severe as to result in resting pain. In the heart, however, even minor reductions in blood flow may immediately elicit chest pain. In other areas of the body, perfusion deficit could lead to permanent tissue impairment or patient death. Also, perfusion deficit in some areas of the body may be immediately harmful, while perfusion deficit in other areas of the body may reveal symptoms with prolonged perfusion deficit.

FIG. 3A is a flowchart of an exemplary method 300 of assessing heart function, according to an exemplary embodiment. The method of FIG. 3A may be performed by server systems 106, based on information, images, and data received from physicians 102 and/or third party providers 104 over electronic network 101.

In one embodiment, step 301 may include receiving a patient-specific anatomic heart model in an electronic storage medium (e.g., hard drive, network drive, cloud drive, mobile phone, tablet, etc.). The patient-specific anatomic heart model may include one or more regions of the patient's left ventricular myocardium and/or the patient's myocardium surrounding one or more of the other heart chambers. In one embodiment, this patient-specific anatomic model may be constructed by extracting a model from one or more medical images (e.g., a CT, MR, ultrasound, SPECT, or PET image).

In one embodiment, step 303 may include receiving a patient-specific anatomic vascular model of one or more sections of the coronary vasculature in an electronic storage medium. In one embodiment, this patient-specific vascular model may be constructed by extracting a model from one or more medical images (e.g., a CT and/or a MR).

In one embodiment, step 305 may include receiving an estimate of blood supplied to one or more areas of the patient-specific anatomic heart model, e.g., under one or more physiological states. For example, an estimate of blood supply may be inferred from measurements taken from imaged data. For instance, a blood flow volume per unit time may be measured with perfusion imaging. This measured blood flow volume per unit time may be treated as an estimate of blood supply, or an estimate of blood supply may be inferred from measured blood flow volume per unit time. Alternately or in addition, a substantial pressure loss from the blood supply source may be treated as an estimate of inadequate blood supply. Receiving the estimate of blood supplied to the patient-specific heart model may include measuring or receiving a measurement of blood supply to the patient's heart, or calculating an estimate of blood supply (e.g., via simulation). This estimate of supplied blood may be determined via several means, for example, measurement from imaging and/or an estimate of a functionally significant compromise of blood flow in one or more blood vessels of the vascular model (e.g., of step 303). Measurement from imaging may include, e.g., measurements via SPECT, PET, MR perfusion, magnetic resonance myocardial perfusion imaging (MRMPI), CT perfusion, or an analysis of wall motion from ultrasound images. In one embodiment, step 305 may include estimating functionally significant compromise of blood flow, based on the received and/or calculated estimate of supplied blood. Estimating functionally significant compromise of blood supply may include assessments, for instance, by an invasive measurement (e.g., FFR, iFR, intravascular ultrasound Doppler, etc.), a blood flow simulation (e.g., using 3D or 1D fluid simulation techniques, transluminal attenuation flow encoding (TAFE), etc.), a blood flow estimate provided by a database, a blood flow estimate determined via a machine learning method, a calculation using imaging characteristics (e.g., transluminal attenuation gradient (TAG) or corrected coronary opacification (CCO)), a (simulated) cardiac event (e.g., a plaque rupture), etc.

In one embodiment, step 307 may include receiving and/or calculating a relationship between the patient's vessels (e.g., of the patient vascular model of step 303) and locations of the patient's heart (e.g., based on the patient-specific heart model of step 301). In other words, step 307 may include determining locations or regions of the patient's heart affected by an estimated blood supply.

In one embodiment, step 307 may include receiving and/or calculating a connection between functionally significant vessels and affected locations of the patient-specific heart model. For example, affected locations of the patient-specific heart model may include locations experiencing an inadequate (e.g., functionally significant) reduction of blood flow (e.g., given by the blood supply estimate of step 305). This may be explained in further detail in FIG. 3B. This connection may be derived through several means, for example: calculating the connection from the vascular model using a microvascular tree generation technique (e.g., constrained constructive optimization), assigning each location in the patient-specific anatomic heart model to the closest location in the vascular model (e.g., by modeling microvascular flow using a fast marching method with front originating from the termination of the vascular model), using a database and/or machine learning methods employing local characteristics from one or more images (e.g., intensity, texture), vessel characteristics (e.g., size, tortuosity), and/or patient characteristics (e.g., gender, age, hypertensive status, smoking status, diabetic status), using a generic population-based model, etc.

In one embodiment, step 309 may include determining, using a processor (e.g., a computer, laptop, DSP, cloud computing, GPU, smartphone, tablet, etc.), one or more assessments of heart function, for example: (1) electrical activation, arrhythmia, tachycardia, and/or fibrillation; (2) ejection fraction (injection fraction), stroke volume, aortic pressure, fractional shortening, cardiac index, and/or cardiac output (cardiac input) of the left or right ventricle and/or combined cardiac output; (3) capacity to perform physical activity; and/or (4) risk of cardiac arrest or sudden death, e.g., heart failure due to reduced ejection fraction or diastolic heart failure.

In one embodiment, an assessment of a patient's heart's electrical activation, arrhythmia, tachycardia, and/or fibrillation may include evaluating one or more tissue characteristics of the patient's heart. For example, an evaluation of tissue characteristics may include estimating the conductance of at least a portion of the patient's heart. Estimating the patient's heart's conductance may include using a simulation performed with a patient-specific electrophysiological model of the patient's heart. For example, the simulation may include assuming that a portion of the heart associated with a limited blood supply (e.g., due to a diseased vessel) may have reduced electrical conductance. The electrophysiological model may include solving the bidomain equations for electrical wave propagation. These equations can be coupled to a continuum tissue mechanics model of active muscle contraction. In some scenarios, the electrophysiological model may be coupled with or used with an electromechanical model of muscle contraction(s). Step 309 may include modeling the reduction in electrical conductance as a function of the reduced blood supply during one or more physiological states. In one case, the patient-specific electrophysiological model of the patient's heart may be based on the patient-specific anatomic heart model (e.g., of step 301), patient characteristics (including family history, age, gender, body size, smoking history, hypertension, and/or diabetic status), etc.

In one embodiment, an assessment of a patient's heart's ejection fraction (injection fraction), stroke volume, aortic pressure, fractional shortening, cardiac index, and/or cardiac output (cardiac input) of the left or right ventricle and/or combined cardiac output may include an evaluation of the contractility of at least a portion of the patient's heart. For example, estimating the heart's contractility may include using a simulation performed with a patient-specific biomechanical model of the patient's heart. For example, the simulation may include assuming that the portion of the heart associated with a limited blood supply (e.g., due to a diseased vessel) may have reduced muscle contractility and/or wall motion during one or more physiological states. Muscle contractility may be modeled using a continuum mechanics model where the properties depend on electrical activity. The reduction in muscle contractility may be modeled as a function of the reduced blood supply. The patient-specific biomechanical heart model may be based on the anatomic heart model (e.g., of step 301), patient characteristics including family history, age, gender, body size, smoking history, hypertension and/or diabetic status, etc.

Alternately or in addition, an assessment of a patient's capacity to perform physical activity may include evaluating the contractility and/or wall motion of at least a portion of the patient's heart. For example, the assessment may involve a patient-specific biomechanical model of the patient's heart (e.g., based on the anatomic heart model (e.g., of step 301), patient characteristics including family history, age, gender, body size, smoking history, hypertension, and/or diabetic status, etc.). For example, the assessment may include assuming that the portion of the heart associated with a limited blood supply (e.g., due to a diseased vessel) may have reduced muscle contractility and/or wall motion. The reduction in muscle contractility may be modeled as a function of the reduced blood supply at one or more exercise states. In one embodiment, step 309 may include estimating cardiac output characteristics (e.g., cardiac output of the left ventricle, the right ventricle, and/or a combined cardiac output) using multiple levels of simulated exercise. Estimating cardiac output characteristics at various levels of simulated exercise may help determine at which level a patient may begin to show an abnormal cardiac output. Such information may be useful in cardiac rehabilitation.

In one embodiment, an assessment of a patient's risk of cardiac arrest or sudden death, e.g., heart failure due to reduced ejection fraction or diastolic heart failure may include evaluating the contractility, wall motion, and/or conductance of at least a portion of the patient's heart. For example, the assessment may involve a patient-specific biomechanical and/or electrophysiological model of the patient's heart (based on the anatomic heart model, patient characteristics including family history, age, gender, body size, smoking history, hypertension and/or diabetic status, etc.). For example, the assessment may include assuming that the portion of the heart associated with a limited blood supply (e.g., due to a diseased vessel) may have reduced muscle contractility, wall motion, and/or electrical conductance. In one embodiment, the biomechanical and electrophysiological models may be coupled or related. In one embodiment, a reduction in muscle contractility and/or electrical conductance may be modeled as a function of the reduced blood supply at one or more exercise states. In one embodiment, step 309 may include estimating cardiac output characteristics (e.g., cardiac output of the left ventricle, the right ventricle, and/or a combined cardiac output) using multiple levels of simulated exercise. Estimating cardiac output characteristics at various levels of simulated exercise may help determine at which level a patient may reach a threshold of inability for their heart to meet the demand of the simulated exercise for the patient's body size (e.g., an ejection fraction less than 40%).

In one embodiment, step 311 may include creating one or more changes to one or more of the anatomical heart, vascular, biomechanical, and/or electrophysiological model(s) to simulate a virtual treatment, for instance, stent insertion, angioplasty, bypass graft, medical therapy (e.g., lipids, beta blockers, increased physical fitness, diet, smoking cessation, etc.), recannulation, embolization, valve replacement, and/or RF or cryo-ablation therapy. The virtual changes may also include a modeling of changes in cross-sectional vessel geometry, for example, vessel narrowing due to disease progression and/or plaque rupture. Virtual changes to the model(s) may further include modeling damage to the vessel due to trauma and/or modeling changes in active or passive mechanical properties of the vessel wall (e.g., vessel wall stiffness).

In such an embodiment, step 311 may further include performing a second determination of a heart function, e.g., based on the modifications to the model to simulate virtual therapy (or virtual disease progression).

FIG. 3A may depict an exemplary flowchart of a method for assessing heart function, and FIG. 3B may provide a more focused, efficient, or rapid way of performing the method of FIG. 3A. For example, FIG. 3B may streamline the method of FIG. 3A by narrowing the assessment of heart function to portions of the heart experiencing or associated with functionally significant compromises of blood flow. The following paragraphs describe FIG. 3B, which depicts an exemplary method of determining a portion of the patient's heart tissue to assess.

FIG. 3B is a flowchart of an exemplary method 320 of determining portions of the patient's heart (e.g., of the patient-specific heart model) for assessing heart function, according to an exemplary embodiment. The method of FIG. 3B may be performed by server systems 106, based on information, images, and data received from physicians 102 and/or third party providers 104 over electronic network 101.

In one embodiment, step 321 may include determining a criteria for functionally significant compromise of blood flow in one or more blood vessels of the vascular model. For example, the criteria may be pre-determined and/or patient-specific. Also, the criteria for functionally significant compromise of blood flow may be based on a patient's physiological state and/or a physiological state determined for the estimate of blood flow. For example, in the scenario that blood flow is determined via a blood flow simulation, the blood flow simulation may be adjusted for one or more physiological states.

In one embodiment, step 323 may include comparing determined blood flow through the vascular model (e.g., of step 305), against the criteria for functionally significant compromise of blood flow to identify one or more blood vessels with functionally significant compromise of blood flow.

In one embodiment, step 325 may include determining one or more portions of the patient-specific heart model (e.g., of step 301) associated with the one or more identified blood vessels. For example, step 325 may include determining portions of the patient-specific heart model adjacent to the one or more identified blood vessels. As discussed earlier, step 325 of determining relationships between the patient-specific heart model and the patient-specific vascular model may include simulating perfusion of blood flow from the patient's vessels to the patient's tissue (e.g., by simulating perfusion of blood flow from the patient-specific vascular model to the patient-specific heart model). Step 325 may further include determining the size of the one or more portions of the patient-specific heart model associated with the one or more identified blood vessels. For example, the portions of the heart model may include the portions of the heart model in contact with the identified blood vessels of the vascular model, or the portion of the heart model experiencing unusual blood flow along with regions of the heart model surrounding that portion.

In one embodiment, step 327 may include determining one of more characteristics of heart function that can be measured from the determined portion of the patient-specific heart model. For example, step 327 may include determining one or more measures of heart function (e.g., electrical conductance, muscle contractility, etc.). Step 327 may further include selecting one or more of the measures of heart function and evaluating the selected measure(s) of heart function for the determined portion of the patient-specific heart model.

FIG. 4A is a flowchart of an exemplary method 400 of assessing muscle function, according to an exemplary embodiment. The method of FIG. 4A may be performed by server systems 106, based on information, images, and data received from physicians 102 and/or third party providers 104 over electronic network 101

In one embodiment, step 401 may include receiving a patient-specific anatomic muscle model in an electronic storage medium (e.g., hard drive, network drive, cloud drive, mobile phone, tablet, etc.). The patient-specific anatomic muscle model may include one or more regions of one or more muscles in the patient's body (e.g., muscles of the patient's leg, hip, shoulder, arm, neck, back, etc.). In one embodiment, this patient-specific muscle model may be constructed by extracting a model from one or more medical images (e.g., a CT, MR, ultrasound, SPECT, or PET image).

In one embodiment, step 403 may include receiving a patient-specific anatomic vascular model of one or more sections of the peripheral vasculature in an electronic storage medium. In one embodiment, this patient-specific vascular model may be constructed by extracting a model from one or more medical images (e.g., a CT and/or a MR).

In one embodiment, step 405 may include receiving an estimate of blood supplied to one or more areas of the patient-specific anatomic muscle model, e.g., under one or more physiological states. Receiving the estimate of blood supplied to the patient-specific heart model may include measuring or receiving a measurement of blood supply to the patient's heart, or calculating an estimate of blood supply (e.g., via simulation). This estimate of supplied blood may be determined via several means, for example, measurement from imaging and/or an estimate of a functionally significant compromise of blood flow in one or more blood vessels of the vascular model (e.g., of step 403). Measurement from imaging may include, e.g., measurements via SPECT, PET, MR perfusion, MRMPI, CT perfusion, or an analysis of wall motion from ultrasound images. In one embodiment, step 405 may include estimating functionally significant compromise of blood flow, based on the received and/or calculated estimate of supplied blood. Estimating functionally significant compromise of blood supply may include assessments, for instance, by an invasive measurement (e.g., FFR, iFR, intravascular ultrasound Doppler, etc.), a blood flow simulation (e.g., using 3D or 1D fluid simulation techniques), a blood flow estimate provided by a database, a blood flow estimate determined via a machine learning method, a calculation using imaging characteristics (e.g., TAG or CCO), a (simulated) cardiac event (e.g., a plaque rupture), etc.

In one embodiment, step 407 may include receiving and/or calculating a relationship between the patient's vessels (e.g., of the patient vascular model of step 303) and locations of the patient's muscles (e.g., based on the patient-specific muscle model of step 401). In other words, step 407 may include determining locations or regions of the patient's heart affected by an estimated blood supply.

In one embodiment, step 407 may include receiving a connection between functionally significant vessels and affected locations of the patient-specific muscle model. For example, affected locations of the patient-specific heart model may include locations experiencing an inadequate (e.g., functionally significant) reduction of blood flow (e.g., given by the blood supply estimate of step 405). This may be explained in further detail in FIG. 4B. This connection may be derived through several means, for example: calculating the connection from the vascular model using a microvascular tree generation technique (e.g., constrained constructive optimization), assigning each location in the patient-specific anatomic muscle model to the closest location in the vascular model, e.g., by modeling microvascular flow using a fast marching method with front originating from the termination of the vascular model, using a database and/or machine learning methods employing local characteristics from one or more images (e.g., intensity, texture), vessel characteristics (e.g., size, tortuosity), and/or patient characteristics (e.g., gender, age, hypertensive status, smoking status, diabetic status), using a generic population-based model, etc.

In one embodiment, step 409 may include determining, using a processor (e.g., a computer, laptop, DSP, cloud computing, GPU, smartphone, tablet, etc.), one or more assessments of muscle function, for example: (1) Capacity to perform physical activity (2) Patient symptoms (e.g., pain after exercise, claudication, etc.), and/or (3) electrical activation, arrhythmia, tachycardia, and/or fibrillation.

In one embodiment, an assessment of a patient's capacity to perform physical activity may include evaluating the contractility of at least a portion of the patient's muscle. For example, the assessment may involve using a patient-specific biomechanical model of the patient's muscle (e.g., based on the anatomic muscle model (e.g., of step 401), patient characteristics including family history, age, gender, body size, smoking history, hypertension, and/or diabetic status, etc.). For example, the assessment may include assuming that the portion of the muscle associated with a limited blood supply (e.g., due to a diseased vessel) may have reduced muscle contractility. The reduction in muscle contractility may be modeled as a function of the reduced blood supply at one or more exercise states. In one embodiment, step 409 may include estimating muscle output characteristics using multiple levels of simulated exercise (e.g., rest, walking, running, etc.). Estimating muscle output characteristics at various levels of simulated exercise may help determine at which level a patient may begin to show an abnormal muscle output. Such information may be useful in patient rehabilitation to assess an appropriate target level of exercise.

In one embodiment, an assessment of a patient symptoms (e.g., pain after exercise, claudication, etc.) may include evaluating the contractility of at least a portion of the patient's muscle. For example, the assessment may involve using a patient-specific biomechanical of the patient's muscle (e.g., based on the anatomic muscle model (e.g., of step 401), patient characteristics including family history, age, gender, body size, smoking history, hypertension and/or diabetic status, etc.). For example, the assessment may include assuming that the portion of the muscle associated with a limited blood supply (e.g., due to a diseased vessel) may have reduced muscle contractility. In one embodiment, a reduction in muscle contractility may be modeled as a function of the reduced blood supply at one or more exercise states. In one embodiment, step 409 may include estimating muscle output characteristics using multiple levels of simulated exercise. Estimating muscle output characteristics at various levels of simulated exercise may help determine if the patient's muscle output is sufficient to support a given level of exercise (e.g., walking) and/or whether the patient may experience pain at a given level of exercise.

In one embodiment, step 411 may include creating one or more changes to one or more of the anatomical muscle, vascular, biomechanical, and/or electrophysiological model(s) to simulate a virtual treatment, for instance, stent insertion, angioplasty, endarterectomy, bypass graft, medical therapy (e.g., lipids, beta blockers, increased physical fitness, diet, smoking cessation, etc.), recannulation, and/or embolization. The virtual changes may also include a modeling of changes in cross-sectional vessel geometry, for example, vessel narrowing due to disease progression and/or plaque rupture. Virtual changes to the model(s) may further include modeling damage to the vessel due to trauma and/or modeling changes in active or passive mechanical properties of the vessel wall (e.g., vessel wall stiffness).

In such an embodiment, step 411 may further include performing a second determination of a muscle function, e.g., based on the modifications to the model to simulate virtual therapy (or virtual disease progression).

FIG. 4A may depict an exemplary flowchart of a method for assessing muscle function, and FIG. 4B may provide a more focused or rapid way of performing the method of FIG. 4A. For example, FIG. 4B may streamline the method of FIG. 4A by narrowing the assessment of muscle function to portions of the patient's muscle tissue experiencing or associated with functionally significant compromises of blood flow. The following paragraphs describe FIG. 4B, which depicts an exemplary method of determining a portion of the patient's muscle tissue to assess.

FIG. 4B is a flowchart of an exemplary method 420 of determining portions of the patient's muscle (e.g., of the patient-specific muscle model) for assessing muscle function, according to an exemplary embodiment. The method of FIG. 4B may be performed by server systems 106, based on information, images, and data received from physicians 102 and/or third party providers 104 over electronic network 101.

In one embodiment, step 421 may include determining a criteria for functionally significant compromise of blood flow in one or more blood vessels of the vascular model. For example, the criteria may be pre-determined and/or patient-specific. Also, the criteria for functionally significant compromise of blood flow may be based on a patient's physiological state and/or a physiological state determined for the estimate of blood flow. For example, in the scenario that blood flow is determined via a blood flow simulation, the blood flow simulation may be adjusted for one or more physiological states.

In one embodiment, step 423 may include comparing determined blood flow through the vascular model (e.g., of step 405), against the criteria for functionally significant compromise of blood flow to identify one or more blood vessels with functionally significant compromise of blood flow.

In one embodiment, step 425 may include determining one or more portions of the patient-specific muscle model (e.g., of step 401) associated with the one or more identified blood vessels. For example, step 425 may include determining portions of the patient-specific muscle model adjacent to the one or more identified blood vessels. As discussed earlier, step 425 of determining relationships between the patient-specific muscle model and the patient-specific vascular model may include simulating perfusion of blood flow from the patient's vessels to the patient's tissue (e.g., by simulating perfusion of blood flow from the patient-specific vascular model to the patient-specific muscle model). Step 425 may further include determining the size of the one or more portions of the patient-specific muscle model associated with the one or more identified blood vessels. For example, the portions of the muscle model may include the portions of the muscle model in contact with the identified blood vessels of the vascular model, or the portion of the muscle model experiencing unusual blood flow along with regions of the muscle model surrounding that portion.

In one embodiment, step 427 may include determining one of more characteristics of muscle function that can be measured from the determined portion of the patient-specific muscle model. For example, step 427 may include determining one or more measures of muscle function (e.g., electrical conductance, muscle contractility, etc.). Step 427 may further include selecting one or more of the measures of muscle function and evaluating the selected measure(s) of muscle function for the determined portion of the patient-specific muscle model.

Vascular disease may cause injury, organ impairment, or even death of a patient. Clinical techniques for assessing vascular disease from observing functional compromise or perfusion deficit are limited because observed data may not provide a clear indication of the relationship between blood supply and tissue function. The present disclosure includes systems and methods for evaluating tissue function by simulating tissue function as a function of measured or modeled blood flow. The systems and methods may provide data on when or what kind of blood flow compromise may impact tissue function, as well as the extent of that impact to the tissue function. Accordingly, the disclosed systems and methods may provide more targeted treatment planning (e.g., pinpointing regions or locations in the patient's anatomy) for employing effective treatment.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of assessing tissue function, the method comprising:
    receiving a patient-specific vascular model generated from patient-specific imaging of at least a portion of a vasculature of a patient;
    computing a blood flow through the patient-specific vascular model;
    estimating a functionally significant compromise of blood flow through at least one vessel of the patient-specific vascular model;
    receiving a patient-specific tissue model generated from patient-specific imaging;
    dividing the patient-specific tissue model into one or more subsections;
    determining a relationship between (a) the at least one vessel having a functionally significant compromise of blood flow and (b) at least one subsection of the one or more subsections of the patient-specific tissue model;
    computing, for the at least one each subsection of the one or more subsections of the patient-specific tissue model, a corresponding perfusion value based on the computed blood flow;
    simulating a treatment of the at least one subsection of the one or more subsections of the patient-specific tissue model by updating the patient-specific vascular model or the one or more subsections at least one subsection of the patient-specific tissue model based on the estimated functionally significant compromise of blood flow and the determined relationship;
    computing an updated perfusion value of the at least one subsection of the patient-specific tissue model of the one or more subsections, using the updated patient-specific vascular model or the updated one or more subsections at least one subsection of the patient-specific tissue model; and
    generating a treatment recommendation for the at least one subsection of the one or more subsections, based on the updated perfusion value of the at least one subsection.

2. The computer-implemented method of claim 1, wherein determining the relationship includes identifying, based on the computed perfusion value, a perfusion deficit in the at least one subsection of the patient-specific tissue model; and wherein the generating the treatment recommendation is based on the identified perfusion deficit.

3. The computer-implemented method of claim 1, further comprising:
conducting an assessment of tissue function based on the computed blood flow or the computed perfusion value.

4. The computer-implemented method of claim 3, wherein the assessment of tissue function includes an assessment of a patient's risk relating to electrical activation, arrhythmia, tachycardia, fibrillation, ejection fraction, stroke volume, aortic pressure, fractional shortening, cardiac index, cardiac output, capacity to perform physical activity, cardiac arrest, pain, claudication, or a combination thereof.

5. The computer-implemented method of claim 3, wherein the assessment of tissue function includes an assessment of one or more patient-specific tissue characteristic values including a measure of electrical conductance, muscle contractility, wall motion, or a combination thereof.

6. The computer-implemented method of claim 1, further comprising:
generating a patient-specific electrophysiological and/or biomechanical model of the patient's tissue as a function of the computed blood flow; and
calculating a patient-specific tissue characteristic value using the patient-specific electrophysiological and/or biomechanical model of the patient's tissue.

7. The computer-implemented method of claim 1, further comprising:
determining a vessel outlet of the patient-specific vascular model, wherein the computing, for the at least one subsection of the patient-specific tissue model, a corresponding perfusion value is based on the determined vessel outlet.

8. The computer-implemented method of claim 1, wherein the treatment recommendation includes an evaluation of stent insertion, angioplasty, bypass graft, drugs, increased physical fitness, diet, smoking cessation, recannulation, embolization, valve replacement, and/or ablation therapy.

9. The computer-implemented method of claim 1, further comprising using machine learning to associate the blood flow with one or more subsections of the patient-specific tissue model.

10. A system for assessing tissue function, the system comprising:
a data storage device storing instructions for assessing tissue function based on vascular disease; and
a processor configured to execute the instructions to perform a method including:
receiving a patient-specific vascular model generated from patient-specific imaging of at least a portion of a vasculature of a patient;
computing a blood flow through the patient-specific vascular model;
estimating a functionally significant compromise of blood flow through at least one vessel of the patient-specific vascular model;
receiving a patient-specific tissue model generated from patient-specific imaging;
dividing the patient-specific tissue model into one or more subsections;
determining a relationship between (a) the at least one vessel having a functionally significant compromise of blood flow and (b) at least one subsection of the one or more subsections of the patient-specific tissue model;
computing, for the at least one each subsection of the one or more subsections of the patient-specific tissue model, a corresponding perfusion value based on the computed blood flow;
simulating a treatment of the at least one subsection of the one or more subsections of the patient-specific tissue model by updating the patient-specific vascular model or the one or more subsections at least one subsection of the patient-specific tissue model based on the estimated functionally significant compromise of blood flow and the determined relationship;
computing an updated perfusion value of the at least one subsection of the patient-specific tissue model of the one or more subsections, using the updated patient-specific vascular model or the updated one or more subsections at least one subsection of the patient-specific tissue model; and
generating a treatment recommendation for the at least one subsection of the one or more subsections, based on the updated perfusion value of the at least one subsection.

11. The system of claim 10, wherein determining the relationship includes identifying, based on the computed perfusion value, a perfusion deficit in the at least one subsection of the patient-specific tissue model; and wherein the generating the treatment recommendation is based on the identified perfusion deficit, determining the relationship includes identifying, based on the computed perfusion value, a perfusion deficit in the at least one subsection of the patient-specific tissue model; and
generating the treatment recommendation based on the identified perfusion deficit.

12. The system of claim 10, wherein the system is further configured for:
conducting an assessment of tissue function based on the computed blood flow or one or more of the computed perfusion value.

13. The system of claim 12, wherein the assessment of tissue function includes an assessment of a patient's risk relating to electrical activation, arrhythmia, tachycardia, fibrillation, ejection fraction, stroke volume, aortic pressure, fractional shortening, cardiac index, cardiac output, capacity to perform physical activity, cardiac arrest, pain, claudication, or a combination thereof.

14. The system of claim 12, wherein the assessment of tissue function includes an assessment of one or more patient-specific tissue characteristic values including a measure of electrical conductance, muscle contractility, wall motion, or a combination thereof.

15. The system of claim 10, wherein the system is further configured for:
generating a patient-specific electrophysiological and/or biomechanical model of the patient's tissue as a function of the computed blood flow; and
calculating a patient-specific tissue characteristic value using the patient-specific electrophysiological and/or biomechanical model of the patient's tissue.

16. The system of claim 10, wherein the system is further configured for:
determining a vessel outlet of the patient-specific vascular model, wherein the computing, for the at least one subsection of the patient-specific tissue model, a corresponding perfusion value is based on the determined vessel outlet.

17. The system of claim 10, wherein the treatment recommendation includes an evaluation of stent insertion, angioplasty, bypass graft, drugs, increased physical fitness, diet, smoking cessation, recannulation, embolization, valve replacement, and/or ablation therapy.

18. A non-transitory computer readable medium for use on a computer system containing computer-executable programming instructions for performing a method of assessing tissue function, the method comprising:

receiving a patient-specific vascular model generated from patient-specific imaging of at least a portion of a vasculature of a patient;

computing a blood flow through the patient-specific vascular model;

estimating a functionally significant compromise of blood flow through at least one vessel of the patient-specific vascular model;

receiving a patient-specific tissue model generated from patient-specific imaging;

dividing the patient-specific tissue model into one or more subsections;

determining a relationship between (a) the at least one vessel having a functionally significant compromise of blood flow and (b) at least one subsection of the one or more subsections of the patient-specific tissue model;

computing, for the at least one each subsection of the one or more subsections of the patient-specific tissue model, a corresponding perfusion value based on the computed blood flow;

simulating a treatment of the at least one subsection of the one or more subsections of the patient-specific tissue model by updating the patient-specific vascular model or the one or more subsections at least one subsection of the patient-specific tissue model based on the estimated functionally significant compromise of blood flow and the determined relationship;

computing an updated perfusion value of the at least one subsection of the patient-specific tissue model of the one or more subsections, using the updated patient-specific vascular model or the updated one or more subsections at least one subsection of the patient-specific tissue model; and generating a treatment recommendation for the at least one subsection of the one or more subsections, based on the updated perfusion value of the at least one subsection.

19. The non-transitory computer readable medium of claim 18, wherein determining the relationship includes identifying, based on the computed perfusion value, a perfusion deficit in the at least one subsection of the patient-specific tissue model; and wherein the generating the treatment recommendation is based on the identified perfusion deficit.

20. The non-transitory computer readable medium of claim 18, the method further comprising:

conducting an assessment of tissue function based on the computed blood flow or the computed perfusion value.

* * * * *

UNITED STATES PATENT AND TRADEMARK OFFICE
CERTIFICATE OF CORRECTION

| | |
|---|---|
| PATENT NO. | : 11,605,466 B2 |
| APPLICATION NO. | : 15/991097 |
| DATED | : March 14, 2023 |
| INVENTOR(S) | : Leo Grady and Charles A. Taylor |

It is certified that error appears in the above-identified patent and that said Letters Patent is hereby corrected as shown below:

In the Claims

In Column 14 Lines 44-45, delete "each" and "of the one or more subsections"
In Column 14 Line 49, delete "of the one or more subsections"
In Column 14 Line 51, delete "one or more subsections"
In Column 14 Lines 56-57, delete "of the one or more subsections"
In Column 14 Lines 58-59, delete "one or more subsections"
In Column 14 Line 62, delete "of the one or more subsections"
In Column 16 Lines 1-2, delete "each" and "of the one or more subsections"
In Column 16 Lines 5-6, delete "of the one or more subsections"
In Column 16 Line 8, delete "one or more subsections"
In Column 16 Lines 13-14, delete "of the one or more subsections"
In Column 16 Lines 15-16, delete "one or more subsections"
In Column 16 Line 19, delete "of the one or more subsections"
In Column 16 Line 36, delete "one or more of"
In Column 17 Lines 23-24, delete "each" and "of the one or more subsections"
In Column 17 Lines 27-28, delete "of the one or more subsections"
In Column 18 Line 2, delete "one or more subsections"
In Column 18 Lines 7-8, delete "of the one or more subsections"
In Column 18 Lines 9-10, delete "one or more subsections"
In Column 18 Line 13, delete "of the one or more subsections"

Signed and Sealed this
Twenty-ninth Day of April, 2025

Coke Morgan Stewart
*Acting Director of the United States Patent and Trademark Office*